United States Patent [19]

Cox et al.

[11] Patent Number: 4,679,144
[45] Date of Patent: Jul. 7, 1987

[54] CARDIAC SIGNAL REAL TIME MONITOR AND METHOD OF ANALYSIS

[75] Inventors: Michael W. Cox, Lincroft, N.J.; Richard I. Levin, New York, N.Y.; David J. Cohen, Sag Harbor, N.Y.; William R. Frisbie, East Hampton, N.Y.

[73] Assignee: Q-Med, Inc., Clark, N.J.

[21] Appl. No.: 642,690

[22] Filed: Aug. 21, 1984

[51] Int. Cl.$^4$ .................... G06F 15/42; G06G 7/60; A61B 5/04
[52] U.S. Cl. .................... 364/417; 128/702; 128/705; 128/710
[58] Field of Search ............ 364/415, 417; 128/702, 128/703, 704, 705, 710, 696

[56] References Cited

U.S. PATENT DOCUMENTS

| | | | |
|---|---|---|---|
| 3,832,994 | 7/1974 | Bicher et al. .................... | 128/703 X |
| 4,023,564 | 5/1977 | Valiquette et al. ................ | 128/704 |
| 4,193,393 | 3/1980 | Schlager ......................... | 128/702 X |
| 4,531,527 | 7/1985 | Reinhold, Jr. et al. ............ | 128/696 |

OTHER PUBLICATIONS

Bonner, R. E., Schwetman, H. D., "Computer Diagnosis of Electrocardiograms, II, A Computer Program for EKG Measurements", *Computers and Biomedical Research*, 1968, pp. 366-386.

Weisner, S. J. et al., "Microprocessor based, Portable Anesthesiology ST—Segment Analyzer", *Proceedings of the Tenth Annual Northwest Bioengineering Conference*, Mar. 1982, pp. 222-226.

*Primary Examiner*—E. A. Goldberg
*Assistant Examiner*—Patrick W. Foster
*Attorney, Agent, or Firm*—Nies, Webner, Kurz & Bergert

[57] ABSTRACT

An apparatus for monitoring EKG information includes a programmable apparatus carried by an ambulatory patient for performing continuous, real-time analyses of EKG information derived from the patient. The apparatus facilitates the determination of the existence of various conditions based on these analyses which portend cardiac complications including myocardial ischemia, and arrhythemia activity and further instructs the patient on the manner of treatment required for the detected condition.

40 Claims, 14 Drawing Figures

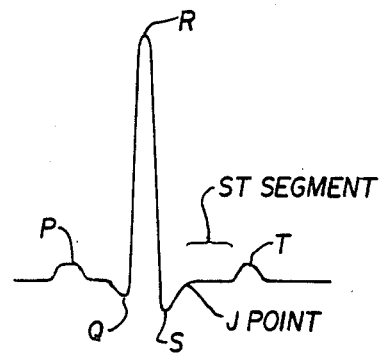
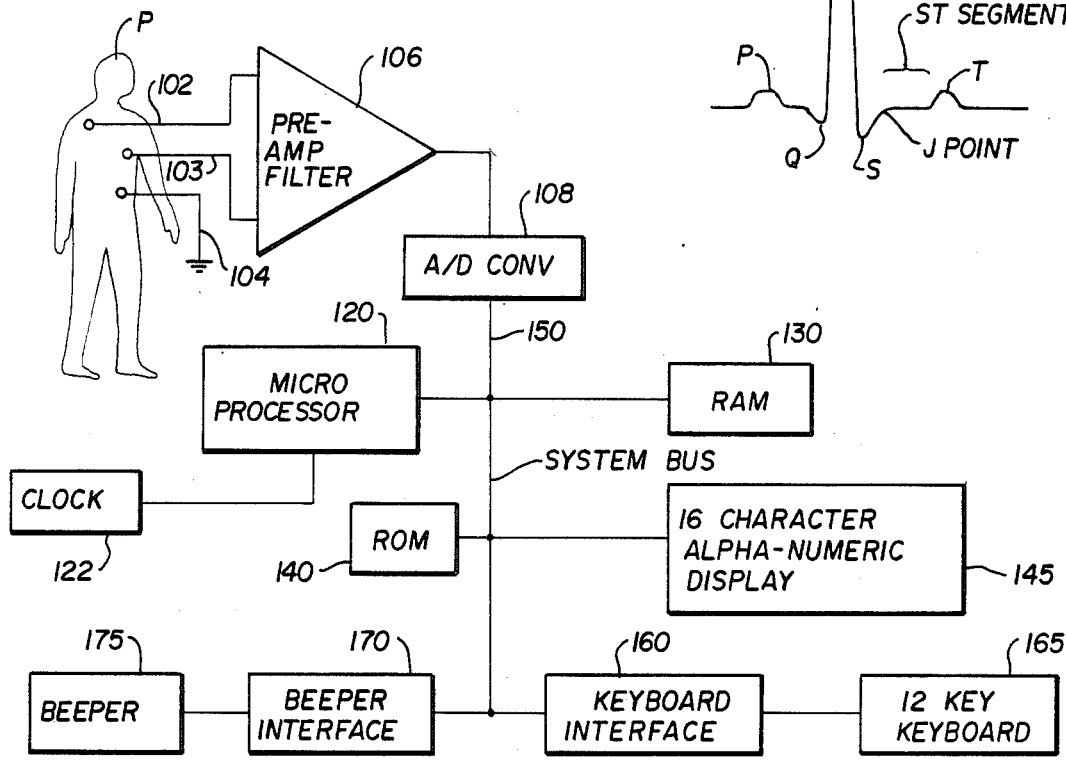
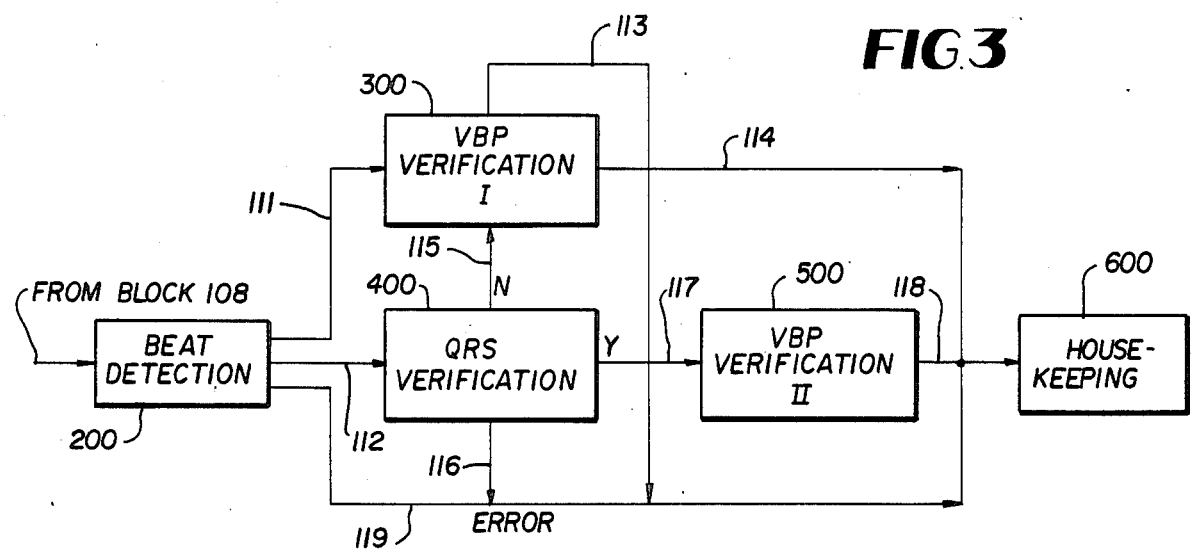

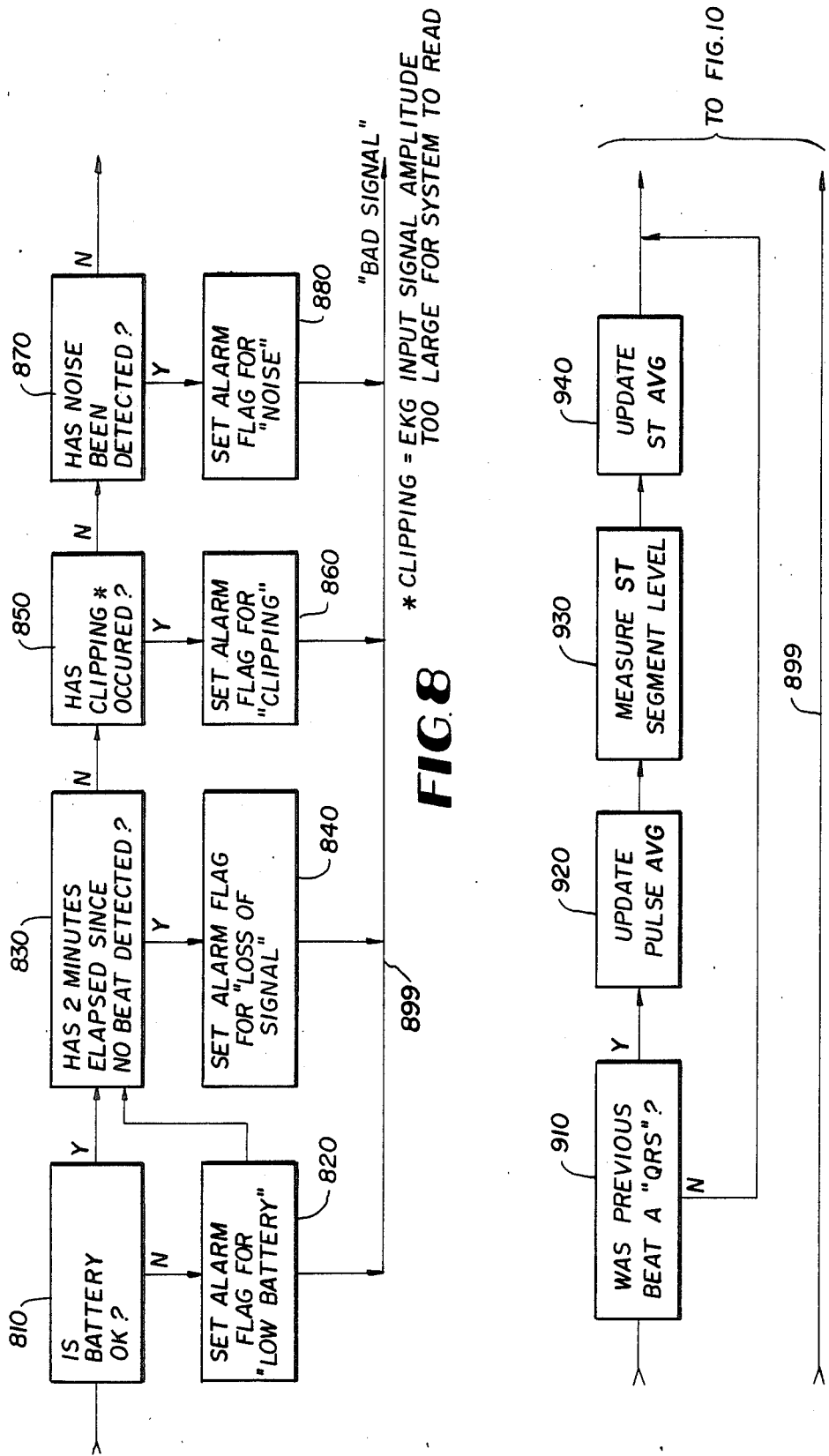

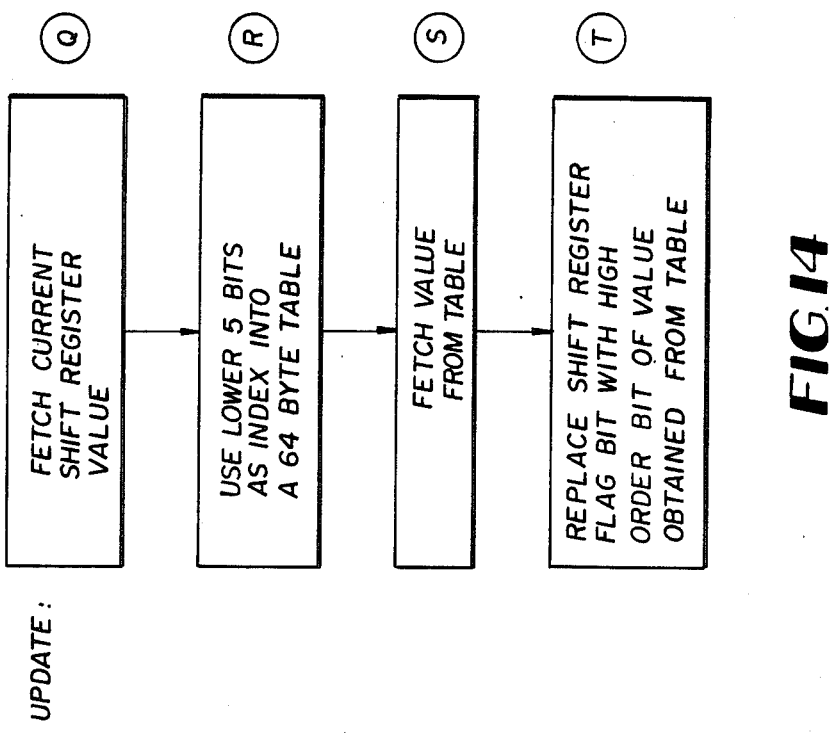
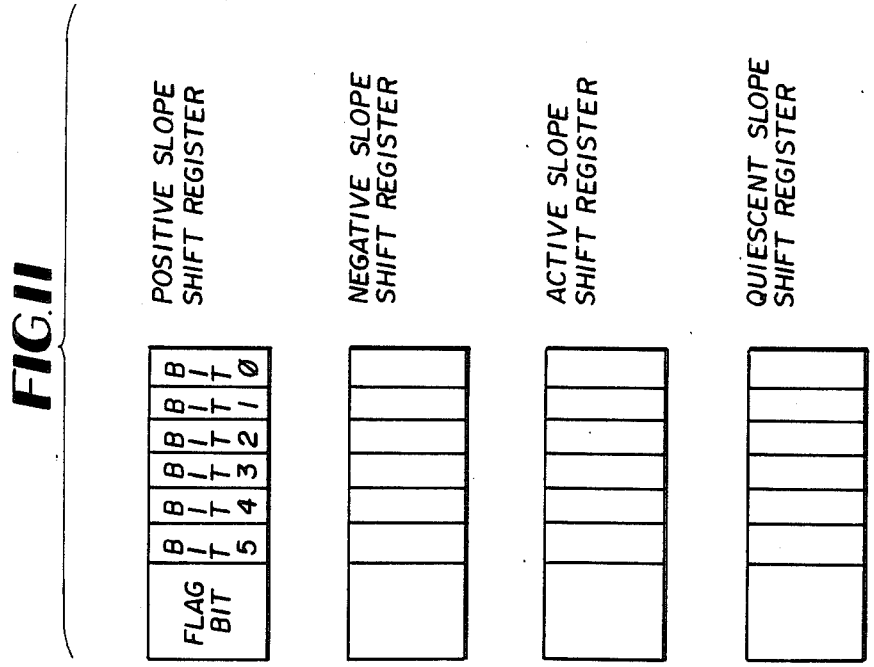

CARDIAC SIGNAL REAL TIME MONITOR AND METHOD OF ANALYSIS

FIELD OF THE INVENTION

The present invention relates to apparatus employed to monitor EKG information, and more particularly relates to a programmable apparatus carried by an ambulatory patient for performing continuous, real-time analyses of EKG information derived from the patient, for determining the existence of various conditions based on these analyses which portend cardiac complications including myocardial ischemia, and arrhythemia activity and for instructing the patient on the manner of treatment required for the detected condition.

BACKGROUND OF THE INVENTION

The leading cause of death in adults in the U.S.A. is coronary artery disease; yet the disease remains silent or dormant in the majority of patients until the fourth or fifth decade of life. Then, coronary artery disease typically moves from the "silent" phase to a symptomatic phase, at which time the patient may experience as the first symtoms, angina pectoris, myocardial infarction, and/or sudden death.

The prevalence of coronary artery disease in the United States has been estimated at over 4,000,000 persons. Over 1,000,000 are expected to have myocardial infarctions each year and of these, approximately 500,000 persons are expected to survive through the first few hours and the subsequent hospitalization. Put another way, a U.S. male has a 1 in 5 chance of having a myocardial infarction or suffering sudden death before the age of 60. Further, once coronary artery disease is symptomatic—regardless of whether the symptom is angina or myocardial infarction—the mortality rate is increased to 4% per year overall and 8% per year in those with an abnormal electrocardiogram or hypertension. This increased mortality is due to sudden death or the complications of repeated myocardial infarction.

Nearly all symptomatic coronary artery disease is due to coronary atherosclerosis, a pathologic process which results in the narrowing of the coronary arteries (the arteries which supply the heart itself with blood) due to the presence of excess cellular and connective tissue materials and an abnormal accumulation of cholesterol. The presence of these narrowings in addition to spasm of the arteries in the area of the narrowings results in an inadequate blood supply to the myocardium or muscle of the heart. This inadequate blood supply is called ischemia and is expressed by a spectrum of conditions including angina, myocardial infarction and sudden death. However, and most significantly, myocardial ischemia may be entirely "silent", i.e. the patient may be totally unaware of a sudden and potentially dangerous decrease in the blood supply to his heart.

Regardless of the initial expression of the coronary artery disease, patients with symptoms are at an increased risk for myocardial infarction and/or sudden death. The current approach to the therapy of this condition has been to make a definitive diagnosis by historical criteria, stress testing, radionuclide studies, and coronary arteriography and then to treat the patient with medication and/or coronary artery bypass surgery. Despite major advances in surgical technique, and the availability of long acting nitrates, betaadrenergic blockers, and calcium antagonists, the death rate from cardiovascular disease has declined only slightly. This suggests the need for new therpeutic approaches.

Traditionally, physicians have recognized the presence of acute myocardial ischemia by noting the occurrence of angina in the patient. Indeed, success of therapy is often gauged by how well the symptom of angina is controlled, i.e. how effective medication or surgery has been at decreasing the frequency and severity of anginal attacks. This is because when angina occurs, it indicates that ischemia is present, and when ischemia is present the chance of myocardial infarction or sudden death is increased. In theory, decrease in attacks of angina should translate into a decrease in myocardial infarction and sudden death; in point of fact, the decrease has been small.

The development of apparatus to perform analyses on electrocardiographic (EKG) signals has facilitated recognition of myocardial ischemia in a patient. Through these analyses it has become widely accepted that a depression of the portion of the EKG signal known as the ST segment, relative to the isoelectric segment of the signal, correlates with partial lack of blood supply, while elevation of the ST segment relative to the isoelectric segment of the signal correlates with a complete lack of blood supply.

Once the ST segment was identified as an indicator of myocardial ischemia, it was then verified that during anginal attacks the ST segment was altered; a deviation of the ST segment could actually precede the experience of angina by several minutes, or even be entirely silent. Silent episodes are no less dangerous then anginal episodes, and occur in patients with equally as extensive coronary disease as those with anginal episodes, and are frequently accompanied by ventricular rhythm disturbances.

An individual patient may express ischemia silently at all times, may have angina during many ischemic episodes, or have both silent and symptomatic episodes. Recently it has been suggested that these silent episodes may be a predictor of myocardial infarction and death.

The patient's failure to sense the myocardial ischemia by experiencing discomfort has been called the result of a defective anginal warning system as it were, and such a defect may be one of the reasons for the high incidence of myocardial infarction and sudden death.

Concern for patients with coronary artery disease and rhythm disturbances has led to the development of various devices for the monitoring of EKG signals. These devices typically are classified into three groups:

(1) devices which record EKG signals continuously for predetermined periods of time on magnetic tape for subsequent printing and analysis by specially trained technicians and/or computers (see U.S. Pat. No. 3,267,934 to Thornton);

(2) devices which analyze the EKG signal as it is generated by the patient and which store selected data for subsequent analysis (see U.S. Pat. Nos. 4,073,001 and 4,006,737 to Cherry et al); and (3) patient activated devices which record, store and or transmit EKG signals to a remote location for analysis when the patient notices something abnormal, or on a preselected basis (see U.S. Pat. No. 3,724,454 to Unger).

The first two groups of devices require sophisticated and costly off-line analysis of large amounts of data which may be available only after the event(s) being monitored has occurred. The third group of devices has the limitations that only symptomatic events detected by the patient are available for analysis, or the preselected schedule established for monitoring signals may permit major EKG events to be missed entirely.

SUMMARY OF THE INVENTION

In summary, starting from this technology, the invention goes forward to provide a portable heart monitoring device which in a real time on-going manner "looks at" each and every heart beat, which analyzes each heart beat for certain abnormalities, and upon detecting a problem or even a potential problem, alerts the user, at the discretion of his physician by programming to the fact, and does so virtually instantly no later than upon completion of that particular suspect heart beat or group(s) of heart beats or ST segment deviations. Because of the data storage and handling abilities and the speed of current computer technology, the invention device in effect gives the patient the benefit of a "cardiologist" who is "diagnosing" each beat of his heart, and who will "prescribe" treatment or recommend other action instantly upon any one of a relatively large number of problems (stored in the computer's memory) arising. The invention is thus a dramatic step forward in the healing arts, and it is expected that the invention will save a large number of lives.

OBJECTS OF THE INVENTION

It is therefore an object of the present invention to provide apparatus which will continuously monitor and analyze EKG or ECG signals generated by an ambulatory patient, diagnose abnormal events and instruct the patient on the manner of treatment required.

Another object of the present invention is to provide a portable computerized EKG monitor for performing real-time analysis of EKG signals to recognize and diagnose myocardial ischemic conditions and thereupon to immediately issue instructions for treatment or other action to the ambulatory user himself.

Another object of the invention is to provide a portable, light-weight computer which performs continuous real-time analysis of EKG information to detect, and alert an ambulatory user of, ischemic conditions, including the silent or pre-symptomatic type.

Another object is to provide a miniaturized EKG computer for identifying ST segment depression or elevation to assist the treatment of myocardial ischemia in an ambulatory patient.

Still another object is to provide a method of analysis of EKG signals which will permit identification of ST depression or elevation indicative of myocardial ischemia, as well as recognition and identification of pulse rate, ventricular tachycardia, and ventricular premature beats.

Yet another object is to provide a method of analysis of EKG signals which will discriminate between valid QRS complex information and information due to noise or artifacts.

These and other objects and advantages are attained by the provision of a device and method of the character described.

BRIEF DESCRIPTION OF DRAWINGS

FIG. 1 is a graphic representation of a typical, normal EKG waveform showing the conventional nomenclature for the various portions thereof;

FIG. 2 is a schematic illustration of apparatus embodying the invention;

FIG. 3 is a master flow chart of the system logic;

FIGS. 8-10 illustrate the logic flow chart of the Housekeeping Block shown in FIG. 3.

FIG. 11 illustrates the use of four shift registers to provide a running record of four slope conditions of an EKG waveform;

FIG. 14 illustrates a logic diagram for updating slope quality shift register Flag Bits.

DETAILED DESCRIPTION OF THE INVENTION

Figure 4:
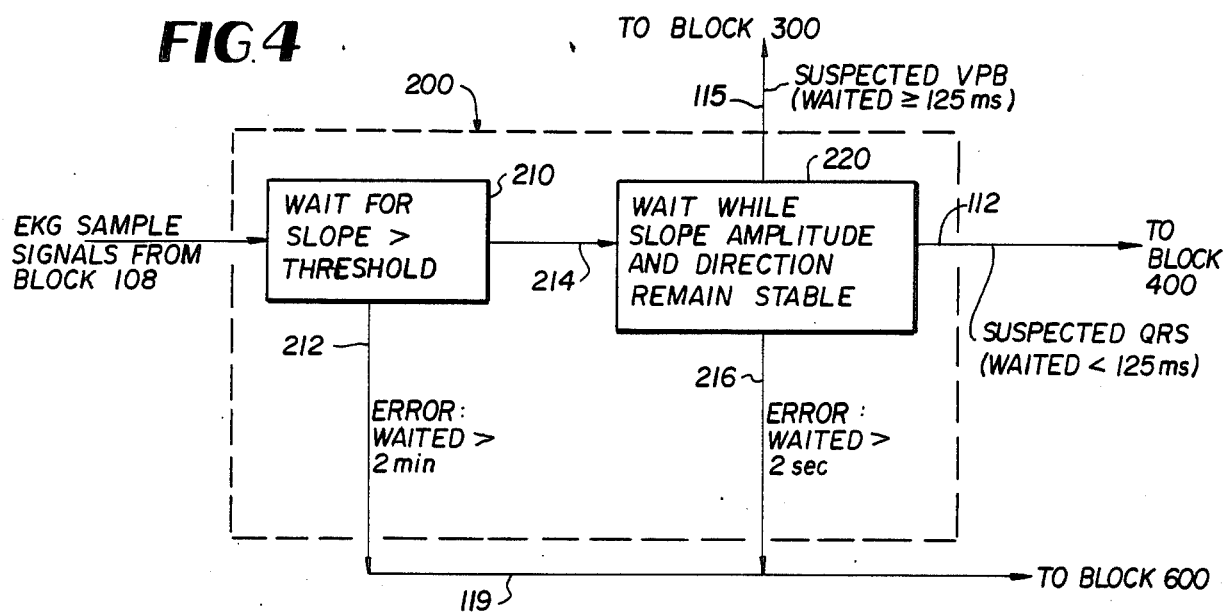
FIG. 4 is a flow chart of the logic of the Beat Detection Block shown in FIG. 3.

Referring now to the drawings in more detail, there is shown in FIG. 1 a typical EKG waveform of a heart of a normal healthy person which exhibits a P wave of positive polarity, a QRS complex consisting of a negative Q wave, a positive R wave and a negative S wave, and finally a T wave separated from the QRS complex by an ST segment. J is a point in the ST segment and defines the end of the S portion thereof.

Normally, in a healthy person the EKG signals will occur regularly at a frequency of about 60-80 beats per minute. Under abnormal conditions the pulse rate may be very erratic. The P wave is normally a small positive wave in certain leads that corresponds to the initial impulse that triggers the commencement of the heartbeat and the resulting reflexive physiological expansions and contractions that are involved in the heart beat. Immediately following the P wave there is a quiescent portion of substantially uniform amplitude. Normally, this portion will have a time duration on the order of greater than 0.04 second and will have a constant or fixed amplitude that may be used as an isoelectric or base line signal. As a result, the amplitude of this portion may be employed as a reference against which the remaining portions of the EKG signal may be measured. Alternatively, the segment just prior to the P wave, the TP segment, may be utilized for definition of the isoelectric amplitude or base line.

At the conclusion of the isoelectric signal, normally after the P wave, the QRS complex occurs. The complex commences in certain ECG leads with a so-called Q wave which is a small negative pulse. The Q wave is succeeded in certain ECG leads by the R wave, which is the most conspicuous portion of the EKG signal. It comprises a positive pulse having an amplitude greater than any of the other waves present in the EKG signal. Normally, the R wave will have the appearance of a "spike" with a sharp rise, a sharp fall, and a relatively short duration. More particularly, it is believed that the maximum time duration will normally be on the order of 0.03 to 0.04 second. However, certain types of abnormalities, such as premature ventricular beats resulting from an ectopic focus (or foci) of depolarization in the ventricle, may result in an EKG signal characterized by a distortion of the R wave and particularly an increase in width thereof. In other forms of premature ventricular beats, the R wave may even become inverted (i.e. of negative polarity).

Following the R wave the QRS complex terminates in an S wave. The S wave may be similar to the Q wave in that it is usually a small negative pulse in certain ECG leads.

Following the QRS complex and the S wave, there will normally be a T wave which is separated from the S wave by the so-called ST segment. The ST segment normally originates at the "J" point which represents the termination of the S wave. The amplitude of this ST segment normally is approximately equal to the isoelectric portion between the termination of the P wave and the commencement of the Q wave, i.e., the ST portion is usually at base line level.

A waveform which is representative of myocardial ischemia may cause the amplitude or level of the ST segment to appear substantially more negative or more positive than the isoelectric portion. An ST segment depression is indicative of an inadequate supply of blood or oxygen to the heart, while an ST segment elevation indicates that the entire heart wall thickness is without adequate blood or oxygen.

Referring now to FIG. 2 there is shown a generalized schematic view of the apparatus of the present invention in which leads 102, 103 and 104 represent electrodes and wires attached to the patient P at predetermined locations preferably in a conventional manner (the preferred embodiment envisions non-intrusive electro-to-patient attachment). The electrodes are preferably of the type disclosed in U.S. Pat. Nos. 3,420,223, 3,490,440 and 3,665,064. Lead 104 functions to ground the apparatus, while leads 102 and 103 feed EKG signals, detected by the electrodes, to a pre-amplifier and filtering component 106 to perform two functions: first, to amplify the signals detected by the electrodes, and second to eliminate undesirable noise. The amplifier, while of conventional design must provide a uniform amount of gain over an adequate bandwidth to effectively amplify all of the components in the EKG signal without producing any distortions so that the output signal from the amplifier is a true and amplified reproduction of the EKG signal picked up by the electrodes.

The output of the amplifier is fed to a converter 108 of the analog-to-digital (A/D) type. The converter is connected, via a system bus 150, to a microprocessor 120 driven by a clock 122 through connection 124, one or more random access memory (RAM) components 130, one or more read only memory (ROM) components 140, an alpha-numeric display device 145, a keyboard 165 and an alarm means 175. A lithium battery can be employed as a back-up for the memory components. A key-board interface component 160 couples keyboard 165 to the system bus 150 while an alarm interface 170 couples alarm means 175 to the system bus. The speeds, capacities, etc. of the hardware components needed to implement the invention can be determined by persons skilled in these arts, based on the teachings herein.

FIG. 3, which is a master logic flow diagram of the present invention, shows the amplified, filtered and digitized EKG signal provided from A/D converter 108 in FIG. 2 passing to beat detection block 200 (to be described in greater detail below). The logic of the beat detection block examines the EKG signal for a suspected QRS complex and for suspected ventricular premature beat (VPB) occurrences. If a pattern of signals which suggests the existence of a VPB is detected, the logic of beat detection block 200 sends appropriate information via lead 111 to the VPB verification logic block 300 (also to be described in more detail below). If a pattern of signals which suggests the existence of a QRS complex is discerned, the logic of beat detection block 200 sends appropriate information via lead 112 to the QRS verification block 400 (also to be described in more detail below). If the logic of block 400 verifies a QRS occurrence, the logic passes to block 500 by line 117 to determine the possible existence of a VPB. On the other hand, if prematurity is detected, the logic passes to block 300 via line 115 to determine whether the suspected signal has further VPB characteristics. The outputs of blocks 300 and 500 are fed via line 114 or line 118, respectively to the housekeeping block 600 (described in more detail below) for further processing. Lead lines 119 (from block 200), 113 (from block 300) and 116 (from block 400) facilitate the transmission of information which is indicative of a discerned error to a system management or "housekeeping" block 600 where, upon its receipt, an alarm may be set off depending on the nature of the event which generates the so-called "error" signal. Examples of such "errors" which could trigger activation of an alarm are disconnection of an electrode, insufficient battery power, battery failure, "loss of signal", excessive noise, and others.

Beat Detection Block 200

FIG. 4 shows the the logic in beat detection block 200. Beat detection block 200 determines the existence of, and discriminates between, two basic signal patterns received from A/D converter 108. These signal patterns are indicative of events which signal the onset of the cardiac complications with which this invention is concerned; one pattern represents the onset and inflection points of QRS complexes, followed by an ST segment, while the other pattern is indicative of ventricular premature beats (VPB's).

Taking a closer look at the beat detection block 200 in FIG. 4, the sequence of amplified, filtered and digitized signal samples are examined at block 210 for a period of time up to, but no exceeding, 2 minutes. In this time frame, the logic of block 210 calculates the slope of the signal values and then compares the slope with a predetermined threshold value. If the slope exceeds the threshold value within the 2 minute period, the logic of block 210 determines that a waveform form indicative of a QRS complex has begun, and the logic proceeds, via line 214, to block 220. If within the two minute interval, the slope does not exceed the threshold valve, the logic of block 210 generates an error signal which passes via lines 212 and then 119 to the system management or housekeeping block 600 to sound an alarm.

After block 210 determines the onset of a slope indicative of a QRS complex, calculations are made at block 220 for the purpose of determining, and therefore confirming, whether a beat actually occurs (if not, the suspected QRS waveform may be a VPB.) The signal sequence is examined at block 220 during the time in which the slope amplitude and direction (sign) remain within specified predetermined tolerances for a maximum of 2 seconds. If the sequence completes in less than 125 milliseconds the logic of block 220 indicates the existence of a suspected QRS waveform, and the process moves to block 400 via line 112. If the change occurs in a time equal to or greater than 125 milliseconds, (and not greater than 2 seconds) the logic of block 220 determines that the sequence of values exhibit characteristics of a VPB, and the logic moves to block 300 for confirmation of the VPB via line 115. If no change occurs within 2 seconds, the logic of block 220 issues an "error" signal which is sent to the system management or housekeeping block 600 via lines 216 and 119.

While waiting for the change in slope direction, the following calculations are made at block 220.

(1) The area beneath the suspected QRS waveform. This value is stored for comparison with the area calculated for the next suspected QRS waveform (in the system management or housekeeping block 600).

(2) The number of turns (i.e. inflection points) in the waveform. This number is compared to predetermined values recognized as being indicative of a normal QRS waveform. Normally, if the number of turns counted falls below 3 or exceeds 5, the waveform is not a QRS waveform and this information is passed to the system management or housekeeping block 600 via lines 116 and 119. More than 5 turns may indicate excessive noise in the system.

(3) The time from one suspected QRS waveform peak to the next suspected QRS waveform peak along the trace. This number is stored for use in identifying (confirming) premature beats, (e.g. VPB's). That is, in a normal sequence of beats, this peak-to-peak distance will be substantially constant. Variation from that constant value usually indicates a VPB.

QRS Verification Blcok 400

Figure 5:
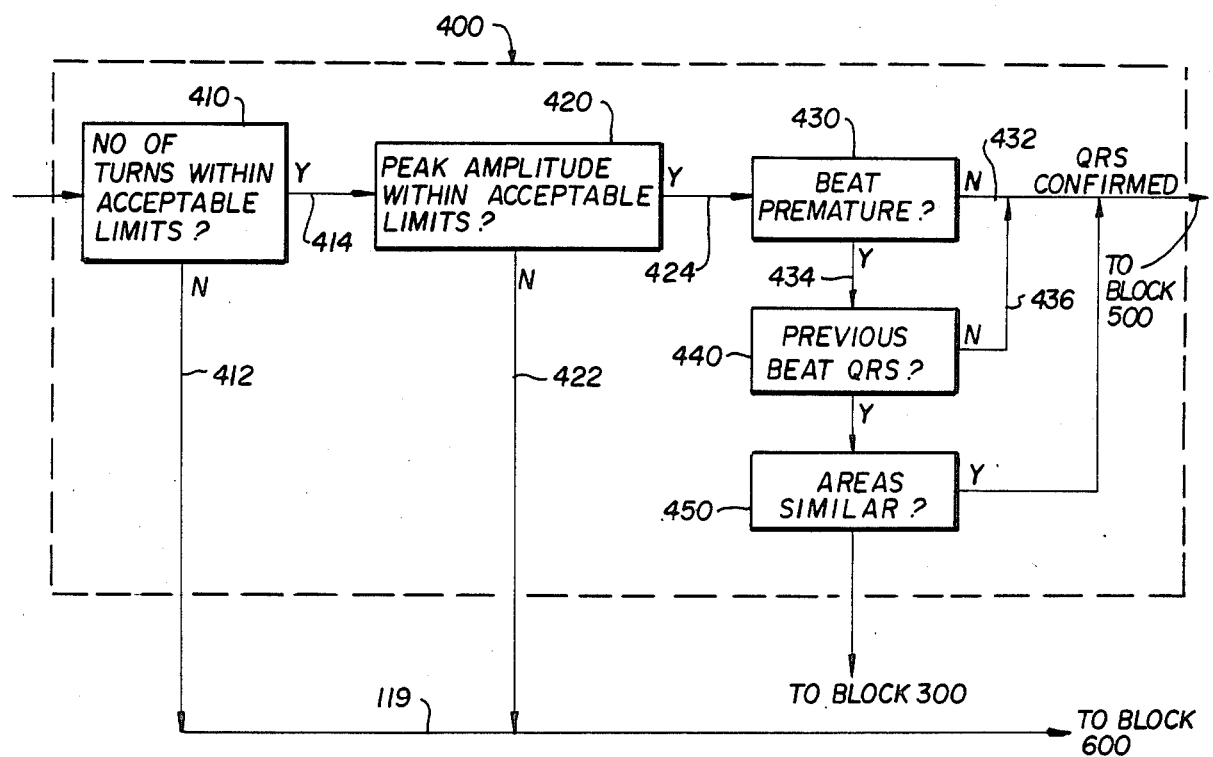
FIG. 5 is a flow chart of the logic of the QRS Verification Block shown in FIG. 3.

Referring now to FIG. 5, the logic flow diagram of the QRS verification block 400 is shown in which the information from block 220 of FIG. 4 is checked to confirm the existence of a QRS waveform. Block 410 counts the turns in the waveform and determines whether the number of turns falls within a range indicative of a normal QRS waveform. If the number of turns counted is less than 3 or greater than 5, the suspected waveform is not a QRS waveform, and this information is passed to housekeeping block 600 via lines 412 and then 119. If the number of turns counted falls within the range of 3, 4 or 5, the logic moves via "yes" line 414 to block 420 where the amplitude of the suspected waveform peak is compared to an empirical value to make sure that the waveform detected by block 200 is a proper QRS curve and not a P wave or a noise pulse or anything else not a QRS. If the peak amplitude does not fall within acceptable limits, an error signal is transmitted via lines 422 and 119 to housekeeping block 600. If it is determined that the peak amplitude falls within acceptable limits, the logic moves to block 430 via line 424 where a determination is made as to whether the waveform generated by the heartbeat is premature. This is accomplished by computing and maintaining a running, updated average of time duration between a series of successive QRS waveform peaks and then comparing the running average time to the time between the current QRS peak and the last QRS peak. In this manner, heart EKG information resulting from both a patient who is exercising and from a patient who is at rest is accommodated. If the logic of block 430 determines that the beat is not premature, a QRS waveform is confirmed and that information is sent to block 500 via line 432. If the logic of block 430 determines that the time between the current and last QRS peak is shorter that the running updated average time, the beat is considered premature (a possible) VPB, and this information passes to block 440 via line 434.

Blocks 440 and 450 perform a secondary check on a suspected QRS waveform which also appears to occur prematurely, i.e. a VPB. For example, without the test provided by blocks 440 an 450 the invention device might otherwise incorrectly identify the end of a waveform in a case where there is an erratic signal portion before the actual termination of the waveform. Block 440 first determines whether the previous beat exhibited true QRS waveform characteristics. The double ended line 436 interconnecting block 440 to line 432 carries the "QRS confirmed" signal. If the previous beat was not a true QRS waveform, there is no proper QRS by which the comparison may be made and the logic returns to line 432. If true QRS waveform characteristics have been detected, and a comparison can be made, the VPB verification logic flows on to block 450 where another check is accomplished by comparing the area under the present waveform to the area under the previous waveform. If the areas are similar, the logic confirms the existence of a proper, albeit premature, QRS waveform and returns to line 432. If the compared areas are not similar, the logic flows to Block 300 (described in detail below) where an analysis is performed to determine whether the waveform is characteristic of a Ventricular Premature Beat (VPB).

VPB Verification Block 300

Figure 6:
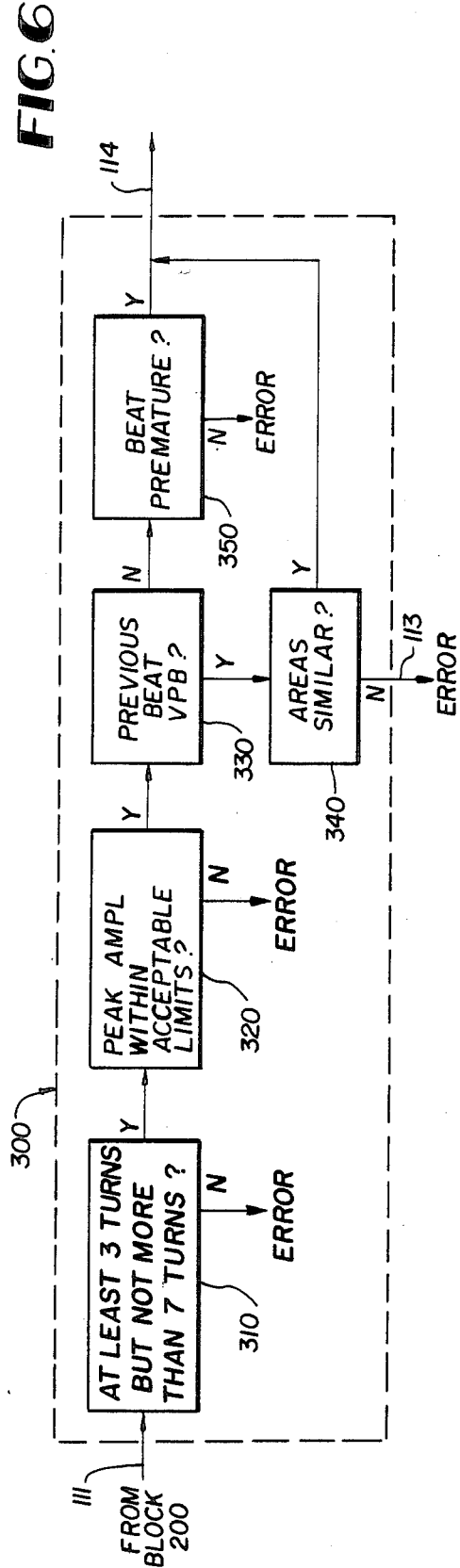
FIG. 6 is a flow chart of the logic of the VPB Verification Block shown in FIG. 5.

Referring now to FIG. 6, there is shown a detailed logic flow diagram for block 300 for the verification of suspected ventricular premature beat waveforms detected at the beat detection block 200 shown in FIG. 4. The logic of block 310 determines whether the number of turns of a curve associated with a heart beat counted at block 220 (FIG. 4) falls within a range indicative of a VPB waveform. If there are at least 3 turns, but no more than 7 turns, then the logic flows to block 320. Whereas 5 turns defined the upper limit for a QRS waveform, the larger number of 7 turns is permitted for VPB verification. If the number counted falls outside this range, block 310 generates an appropriate "error" signal which is sent to housekeeping or system management by Block 600.

The logic of block 320 compares the peak amplitude of the suspected VPB waveform with empirical values indicative of upper and lower acceptable limits in a manner similar to that comparison performed in block 420 (see FIG. 5). If the peak amplitude of the waveform falls outside the range, an error signal is generated and sent to housekeeping block 600. If the peak amplitude falls within the range of acceptable limits, the logic flows to block 330 where the previous beat is examined to determine if it too was a VPB. If the previous beat was not a VPB, block 350 determines whether the current beat is premature. If so, the information is sent to the system management or housekeeping block 600 via line 114. If not, an error signal is sent to the system management or housekeeping block 600. If the logic of block 330 determines that the previous beat was a VPB, it is not possible to check prematurity of the current beat for obvious reasons. Instead block 340 compare the area under the waveform associated with the last beat with the area under the waveform associated with the current beat. This comparison is made with the expectation that the areas will be similar. If the areas are not similar, the logic sends an "error" signal to system management or housekeeping block 600 via line 113. If the areas are similar, the logic returns to line 114 and then to system management or housekeeping block 600.

VPB Verification Block 500

Figure 7:
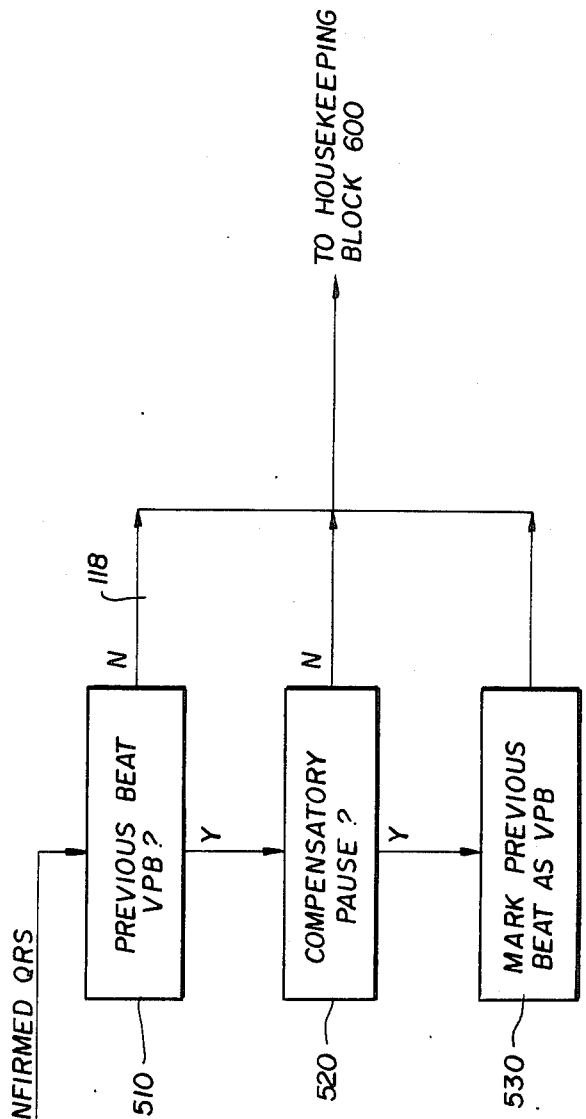
FIG. 7 is a logic flow chart of the VPB Verification Block shown in FIG. 3.

Referring now to FIG. 7, there is shown a detailed logic flow chart of the VPB Verification Block 500 which checks to see whether the waveform confirmed by block 400 was preceded by a VPB. In a case where a QRS waveform follows a ventricular premature beat, the interval between the QRS waveform and the premature beat will be greater than the running updated average time interval computed at block 430 (in FIG. 5).

Block 510 determines if the previous beat was a suspected VPB. If not, control is transferred to system management or housekeeping block 600 via line 118. If the previous beat was a suspected VPB, the compensatory interval is calculated for the purpose of checking for the presence of a compensatory pause which would indicate that the suspected VPB was a true VPB. The current average pulse interval is added to the time at which the QRS complex preceding the suspected VPB is known to have occurred. This result represents a point in time at which a normal beat following a VPB would fall if a compensatory pause were present. If the current beat's time diverges from the calculated time by more than ±12.5% of the current average pulse interval, a compensatory pause is not indicated. The foregoing procedure is repeated three (3) additional times with the average pulse interval being added to the previously calculated compensatory interval each time. This procedure allows for the verification of interpolated VPB's as well as the possibility of verification of VPB's which are followed by "undetected" QRS complexes. If no verification can be made by the end of the fourth (4th) attempt, control is transferred to line 118. If verification is possible, control is transferred to block 530 where the suspected VPB is labelled a confirmed VPB.

System Management or Housekeeping Block 600

Figure 10:
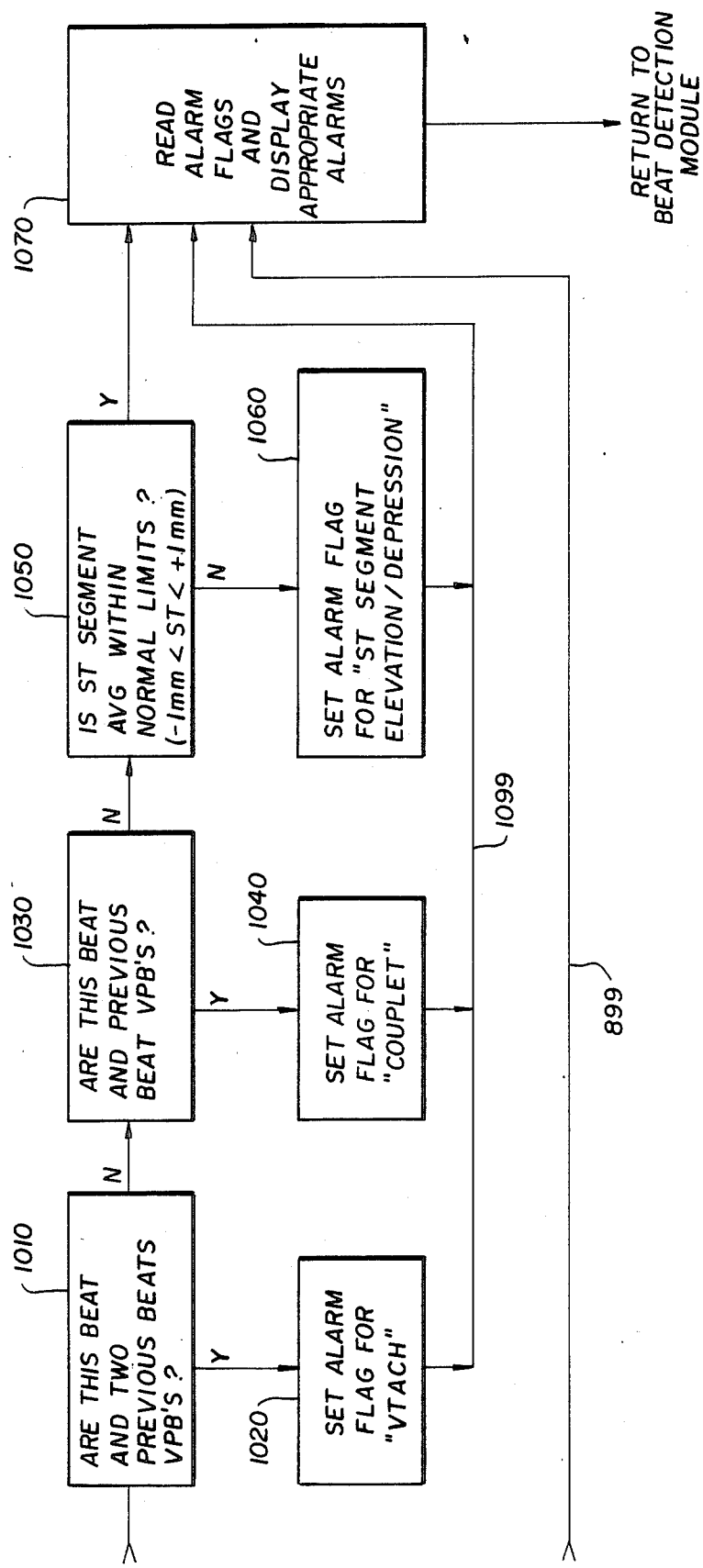

The logic of the system management or housekeeping block 600, illustrated in FIGS. 8-10, performs several functions:

(a) certain events (described in more detail below in connection with FIG. 8) which require the suspension of normal beat processing are monitored;

(b) specified parameters are updated or measured (described in more detail below in connection with FIG. 9);

(c) certain events which trigger conditions are identified and appropriate alarm instructions are issued (described in more detail below in connection with FIG. 10).

As shown in FIG. 8, the logic of block 810 tests whether the power supply is at an acceptable level, i.e. of sufficient voltage to maintain operation of the inventive device. The test is performed by conventional means not shown. If the level of power is not acceptable, the logic of block 810 moves to block 820 where an alarm flag is set for "LOW BATTERY". This information is passed via line 899 to the alarm block 1070 in FIG. 10, while the logic flows to block 830. If the level of power is determined to be acceptable, the logic moves directly to block 830 where it is determined whether there has been a loss of the signal. This condition results from the failure of the device to detect a heartbeat for a period of 2 minutes, and generally is caused by system or patient failure. If, within, the two minute interval, no signal has been detected, the logic moves to block 840 where an alarm flag is set for a "LOSS OF SIGNAL" condition. This information is then passed via line 899 to the alarm block 1070 (shown in FIG. 10). If a beat has been detected within 2 minutes, the analysis proceeds to block 850 where the logic determines whether "SIGNAL CLIPPING" has occurred. If so, the analysis moves to block 860 where an alarm flag is set for a "CLIPPING" condition, and the information is sent via line 899 to alarm block 1070 (shown in FIG. 10). If the logic fails to discern the existence of "SIGNAL CLIPPING", the analysis moves to block 870 where a determination is made whether "NOISE", i.e. a condition exhibiting excessive changes in slope, has been detected. If so, the analysis moves to block 880 where an alarm flag is set for a "NOISE" condition and a signal corresponding to this condition is sent to alarm block 1070 (shown in FIG. 10). If no noise has been detected, the analysis proceeds to block 910 (in FIG. 9) where the system determines whether a QRS waveform accompanied the previous beat. If not, the analysis proceeds directly to block 1010 in FIG. 10. If so, however, the analysis moves successively to blocks 920, 930 and 940. At block 920 the pulse average is updated, at block 930 the ST segment level is measured, and at block 940 the ST segment average is updated. The analysis then moves to block 1010 in FIG. 10, where the logic looks at the results of the analysis performed for the current beat and the last two beats to determine whether all 3 beats exhibits VPB characteristics. If they do, the analysis moves to block 1020 where an alarm flag is set for a condition indicative of Ventricular Tachycardia and this information is sent to Alarm Block 1070 via line 1099. If the 3 beats examined at block 1010 do not exhibit VPB characteristics, the analysis proceeds to block 1030 where the results of the analysis performed for only the current beat and the last beat are examined. If the logic determines that for both beats VPB characteristics were exhibited, the analysis moves to block 1040 where an alarm flag is set for a condition known as "COUPLET" and an appropriate signal is passed to block 1070 via line 1099; otherwise the analysis moves to block 1050 where the logic determines if the ST segment average is within acceptable limits. These limits are empirical values determined for any beat as a function of the isoelectric portion of the PQRST waveform associated with that beat. If the measured ST segment value falls within the limits, the logic proceeds to block 1070. If the measured ST segment value falls outside the limits, the logic moves to block 1060 where an alarm flag is set to reflect either a condition for "ST SEGMENT DEPRESSION" or "ST SEGMENT ELEVATION", and a signal corresponding to the condition detected is sent to alarm block 1070 via line 1099.

Block 1070, which receives information passed through block 1050 from line 1099 and from line 899, and then reads the alarm flags set and displays alarms corresponding to the various detected conditions of the device and the patient. In addition, block 1070 updates the stored counts for VPB couplets, ventricular tachycardia episodes and their total duration, as well as the total ST segment duration. The logic then returns to the beat detection block 200.

The method of determining the significance of the slope signal at each sampling period carried out by the logic of block 210 is explained below with reference to FIGS. 11-14. This method of handling data and determining a slope is deemed to have general utility beyond the present invention.

This method is accomplished using four shift registers each having six bits length (see FIG. 11). Of course, this portion of the invention can also be carried out by using shift registers of longer or shorter length, or even with a different number of shift registers. The patterns in these shift registers reflect slope conditions. Each bit represents one of four conditions at each sampling period and thus each shift register contains a running record of the most current six sampling periods. The four conditions are:

positive slope (upwardly directed)
negative slope (downwardly directed)
active slope (greater than threshold)
quiescent slope (less than threshold)

Each shift register bit will have either (1) a value of 1 (bit set) which indicates that the approximate condition is fulfilled, or (2) a value of 0 (bit reset) which indicates that the respective condition has not been fulfilled. Each shift register also includes a "Flag Bit". This bit is updated after each sampling period and reflects either a majority of bits set, (Flag Bit set) or a majority of bits not set (Flag Bit reset) in the corresponding shift register. A Flag Bit which is set thus represents a trend in slope direction or magnitude.

Figure 12:
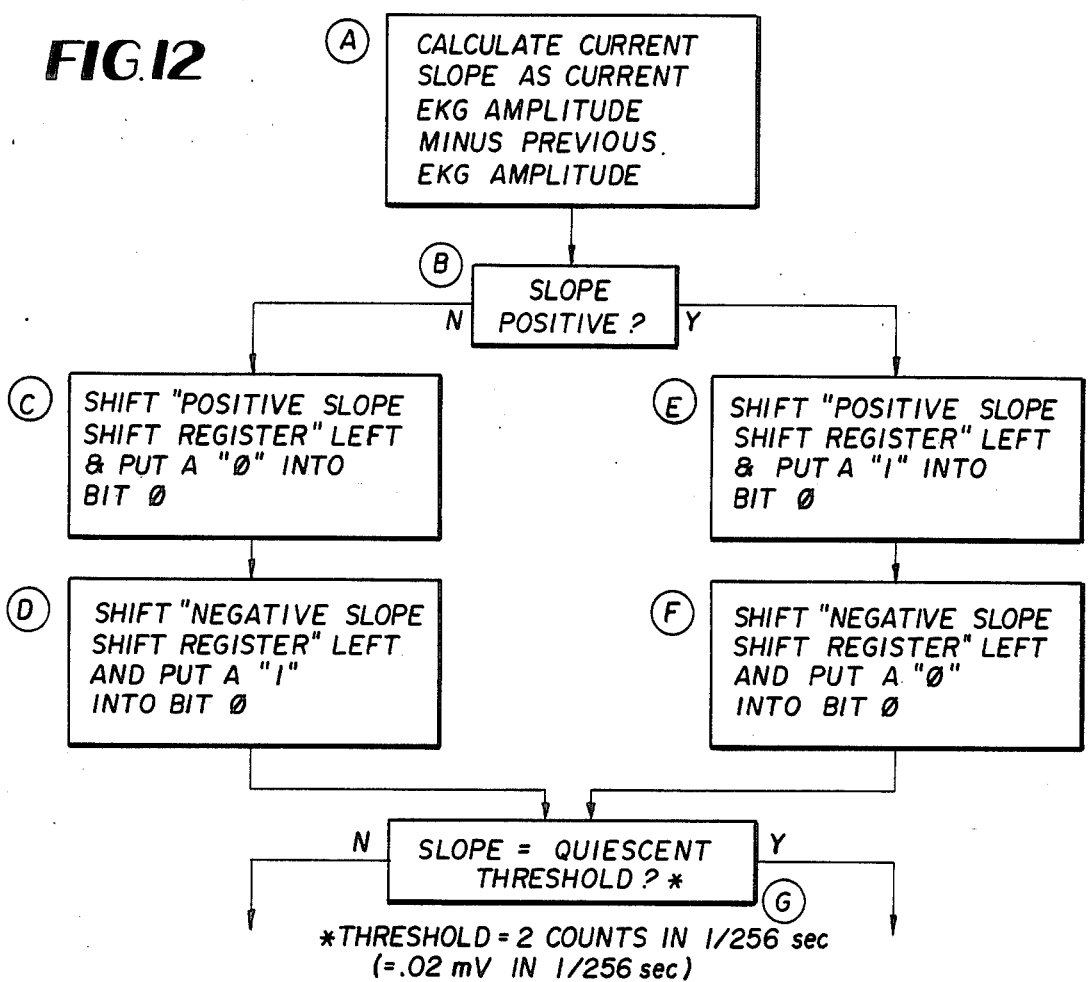
FIGS. 12 and 13 illustrate logic diagrams for using the shft registers to indicate the four slope conditions of the EKG waveform.
Figure 13:
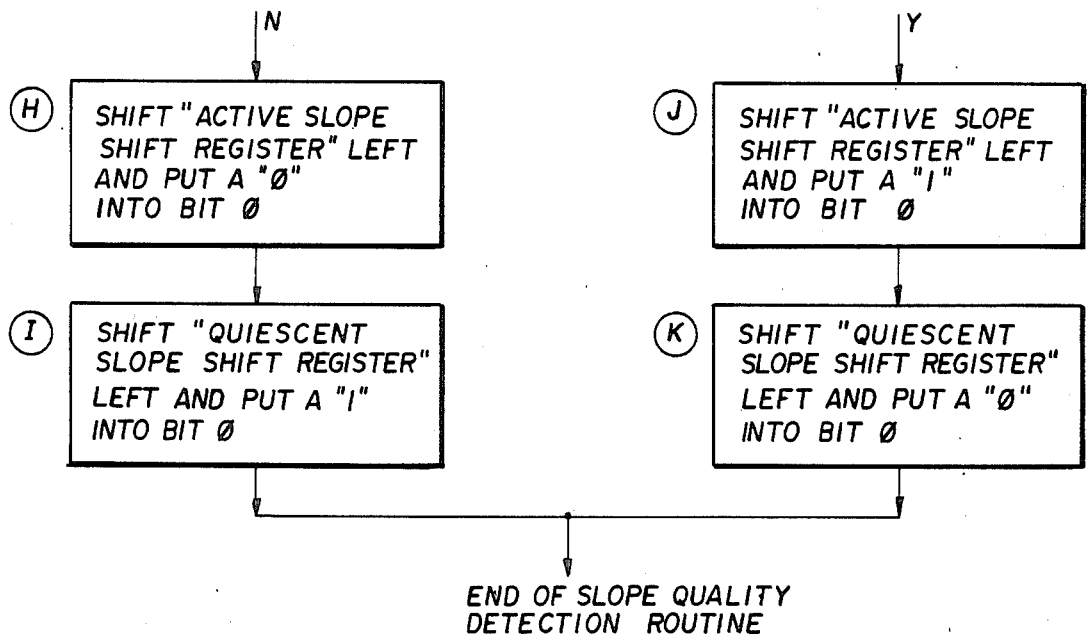

Referring now to FIGS. 12-13, at Block A the slope for the current EKG sample is calculated in accordance with the equation:

CURRENT SLOPE=CURRENT EKG AMPLITUDE MINUS PREVIOUS EKG AMPLITUDE

At Block B, the slope is examined to determine whether the value is positive or negative.

If the slope has a negative value, the logic first proceeds to Block C where the positive slope shift register is shifted to the left and the rightmost bit is set to zero, and then proceeds to Block D where the negative slope shift register is shifted to the left and the rightmost bit is set to 1.

If, however, the slope has a positive value, the logic first proceeds to Block E where the positive slope shift register is shifted to the left and the rightmost bit is set to 1, and then proceeds to Block F where the negative slope shift register is shifted to the left and the rightmost bit is set to zero.

After shifting the appropriate slope registers and setting the appropriate bits corresponding to a detected positive or negative slope value, the logic proceeds to block G where the quantitative aspect of the calculated slope value is compared to the value which represents the predetermined quiescent threshold. (The quiescent threshold is generally taken to be 0.02 millivolts change in each 256th of a second period.) This value differentiates waveforms which represent QRS complexes from other waveforms with which this method is not concerned.

If the value of the slope is less than the quiescent threshold, the logic proceeds (continue to FIG. 13) first to Block H where the active slope shift register is shifted to the left and the rightmost bit is set to zero, and then proceeds to Block I where the quiescent slope shift register is shifted to the left and the rightmost bit is set to 1.

On the other hand, if the value of the slope is greater than, or equal to, the quiescent threshold, the logic proceeds first to Block J where the active shift register is shifted to the left and the rightmost bit is set to 1, and then proceeds to Block K where the quiescent slope shift register is shifted one bit to the left and the rightmost bit position is set to zero.

After completing the operations at either Block I or Block K the Flag Bit for each register is updated to indicate a trend (Flag Bit set to 1) or absence of trend (Flag Bit set to 0).

Next, referring to FIG. 14, the procedure for updating slope quality shift register Flag Bits is described (this procedure is performed four times, once for each shift register).

Overall, this invention uses the fact that six or some other number of positions in a shift register also represent a number, and the fact that machines are very quick at "looking up" numbers in a table. Thus, with a possibility of 1 through 64 possible answers for six bit positions, corresponding to the numbers 0-63, the invention provides a table stored in the machine, certain numbers of which correspond to certain realities of the slope and of the threshold. Thus, the machine can look at the contents of each shift register every 256th part of a second, look at the number, look it up in the table, and thereby quickly determine the quality of the slope as to positive or negative, the threshold exceeded or not exceeded, and set the Flag Bits accordingly.

More specifically, to implement this concept the bits are used as an index, i.e., a six bit binary word will correspond to one of 64 addresses in a 64 byte table (Block R). For 5 or 7 bit shift registers, the addresses and other parameters would be adjusted accordingly.

This table is stored in memory and contains 64 entries, each of which corresponds respectively to each of the 64 six bit binary words which may be used to address the table. Each entry represents whether a majority or minority of bits, in the corresponding six bit word obtained from one of the shift registers, have been set, i.e. have a value of 1. The value of the High Order Bit of each entry is either set (i.e. assigned the value of 1) if a majority of bits in the six bit word have been set, or reset (assigned the value of 0) if a majority of bits in the six bit word have not been set. Thus the High Order Bit will have a value=0 for the first six entries, but will have a value=1 for the eighth entry.

Using the six bit binary address obtained from the respective shift register being updated, a value is retrieved from the table (Block S in FIG. 14). This value is used as a replacement for the Flag Bit of the shift register being updated (Block T).

After the shift registers have been updated as described above, the values of the Flag Bits are examined to detect the following conditions:

BEAT ONSET- indicated when the active slope shift register Flag Bit changes from zero to one, and the negative slope or positive slope shift register flag equals 1.

BEAT TURN- indicated when the active slope shift register Flag Bit remains set (i.e. equal to 1) but Flag Bits of positive and negative slope shift registers change. This indicates a change in slope direction.

BEAT END- indicated when the quiescent slope shift register Flag Bit changes from zero to one.

NOISE- indicated when the active slope shift register Flag Bit is set, but neither the positive slope shift register Flag Bit, nor the negative slope shift register Flag Bit, is set.

Upon the completion of operations in Block 210 of the Beat Detection Block in which the onset of a slope indicative of a QRS complex is identified, the logic proceeds to Block 220, as described above.

It is to be understood that the present invention is not limited to the embodiments disclosed which are illustratively offered and that modifications may be made without departing from the invention.

What is claimed is:

1. A method of evaluating a curve having a rapidly changing value by determining the positive or negative quality of the slope of said curve and by determining when the value of said curve is above or below a predetermined threshold value, comprising the steps of:

determining a frequency of sampling;

determining the slope of the curve between a first sampling and a successive later sampling by substracting the value of the curve at each first sampling from the value of the curve at said later sampling;

providing four shift registers each having space for a plurality of bits and for a Flag Bit;

assigning a shift register to each of the curve values of positive slope, negative slope, above threshold and below threshold;

feeding an appropriate bit value to each shift register at each sampling;

determining a numerical value represented by said plurality of bits arrayed in each shift register;

providing a table of values correlating the status of said Flag Bit to each one of the numerical values possibly represented by said array of bits;

finding said determined numerical value in said table;

changing, as needed, the status of said Flag Bit in accordance with said determined numerical value found in said table; and performing at each sampling said sequence of steps so that the status of said Flag Bit may be changed as needed.

2. The method for continuously monitoring every beat of the heart of a human patient subject to detect abnormal functioning of the heart and to alert the patient immediately upon the occurence of any one of a plurality of detected abnormal heart functions, comprising the steps of:

providing electrode means, using the output signal of said electrode means to produce EKG signals, determining, by analyzing said signals, whether or not each heart beat includes an abnormal QRS portion, determining, by analyzing said signals, whether or not each heart beat is a VPB, and continuously repeating each of said determining steps without interruption while actuating alarm means no later than upon conclusion of said each beat if either of said determining steps indicates an abnormal QRS portion or a VPB, which in turn indicates some abnormal heart function, and signalling to said patient instructions for treatment of each indicated abnormal heart function as it occurs.

3. A portable computerized EKG monitir, comprising:

real-time recognition means for recognizing abnormal cardiac events in an ambulatory patient, real-time diagnosis means for diagnosing each said recognized abnormal cardiac event, and signalling means for communicating to the ambulatory patient a treatment for said recognized and diagnosed abnormal cardiac event.

4. A portable cardiac monitor for an ambulatory patient comprising:

computer means for performing continuous real-time analysis of EKG information derived from said patient, including first means for recognizing abnormal cardiac events, and second means for diagnosing each of said abnormal cardiac events, and means for signalling, to the patient, a treatment corresponding to each said recognized and diagnosed abnormal cardiac event at the onset of each of said abnormal cardiac events, whereby the patient may immediately begin self-treatment of each said recognized and diagnosed abnormal cardiac event without the need for intervention of a trained cardiac specialist.

5. Portable apparatus for continuously monitoring EKG signals generated by the heart of an ambulatory patient, comprising:

self-contained, computerized analyzing means, carried on said patient, for performing real-time analysis of said EKG signals, said computerized analyzing means including means for diagnosing abnormal cardiac events and means for issuing instructions, to said patient, for treatment of said abnormal events.

6. Portable apparatus for continuous real-time monitoring of EKG signals from an ambulatory patient, comprising:

means for detecting, amplifying and digitizing said signals, means for analyzing said digitized signals to determine the existence of abnormal heart conditions;

means for correlating information resulting from analysis of said signals with apparatus condition, and patient treatment, instructions, and means for signalling, to said ambulatory patient, said instruments.

7. The portable apparatus of claim 6, wherein said analyzing means comprises first means for recognizing sequences of signals indicative of waveforms associated with QRS complexes and ventricular premature beats (VPB's) and second means for recognizing sequences of signals associated with apparatus malfunction.

8. The portable apparatus of claim 7, wherein said first recognizing means comprises means for identifying a suspected QRS, or VPB, waveform associated with each heart beat and means for confirming said suspected QRS, or VPB, waveform.

9. The portable apparatus of claim 8, wherein said identifying means comprises first means for determining updatable slope values for successive digitized signals, second means for determining whether each said slope value exceeds a predetermined threshold value, third means for determining whether the sign of the slope value changes within a first predetermined time, and means for comparing the time interval between the onset of said suspected waveform and the occurrence of said slope sign change, said means for comparing being operative only if said first predetermined time is not exceeded.

10. The portable apparatus of claim 9, wherein said identifying means further comprises fourth means for determining whether said time interval is less than a second predetermined time, and means in said correlating means comprises first means for assigning a value to that sequence of signals indicative of a suspected QRS waveform if said first predetermined time is not exceeded and said time interval is less than said second predetermined time.

11. The portable apparatus of claim 10, wherein said first predetermined time is 2 seconds and said second predetermined time is 125 milliseconds.

12. Portable apparatus for continuous real-time monitoring of EKG signals from an ambulatory patient, comprising:
   electrode means for detecting said EKG signals;
   means for amplifying and digitizing the EKG signals detected by said electrode means,
   means for analyzing said digitized signals and identifying abnormal events, and
   means for instantaneously instructing said patient to proceed in a manner corresponding to the abnormal event identified.

13. The portable apparatus of claim 12, wherein said abnormal events include both cardiac events and events associated with operation of the monitor, and said analyzing means includes means for discriminating between said events.

14. The portable apparatus of claim 13, wherein said analyzing means further includes means for detecting the onset of QRS complex waveforms.

15. The portable apparatus of claim 14, wherein said detecting means comprises first means for calculating the slope of said digitized signals, first means for determining whether the calculated slope has exceeded a predetermined threshold valve, second means for determining whether the sign of the slope has changed within a first predetermined time, and third means for determining the interval of time occurring between the slope exceeding said predetermined threshold value and the sign of said slope changing, said third determining means being operative only if said first predetermined time is not exceeded.

16. The portable apparatus of claim 15, wherein said identifying means comprises means for comparing said time interval to a second predetermined time, and means for assigning a first value to a condition in which said time interval is less than said second predetermined time.

17. The portable apparatus of claim 16, wherein said identifying means comprises means for comparing said time interval to a second predetermined time, and means for assigning a second value to a condition in which said time interval is greater than, or equal to, said second predetermined time.

18. The portable apparatus of claim 12, wherein said electrode means comprise electrodes, said electrodes each being defined by claim 1 of any one of U.S. Pat. Nos. 3,420,223 3,490,440 or 3,665,064.

19. The portable apparatus of claim 10, wherein said correlating means further comprises second means for assigning a value to that sequence of signals indicative of a suspected VPB wave form if the first predetermined time is not exceeded and said time interval is equal to or greater than said second predetermined time.

20. The apparatus of claim 19, wherein said first predetermined time is 2 seconds and said second predetermined time is 125 milliseconds.

21. A method for determining cardiac conditions of an ambulatory patient using apparatus carried on the patient including electrode sensing means located in the vicinity of the patient's heart and capable of picking up waveforms corresponding to heartbeats, signal processing means for identifying at least an EKG signal pattern characteristically including an isoelectric baseline portion, a spike portion and a generally linear portion following said spike portion at approximately the same level as said isoelectric portion, a computer means, and a display alarm means actuated by said computer means, the method comprising the steps of:
   sampling a number of said waveforms picked up by said electrode means,
   detecting, in said waveforms, distortions from said EKG signal pattern indicative of abnormal cardiac conditions,
   distinguishing between a first distortion pattern characterized by a variation in the peak-to-peak distance between each spike of said waveforms and indicative of a ventricular premature beat, and a second distortion pattern characterized by a deviation of said linear portion from the level of said isoelectric portion in at least one of said waveforms and indicative of a myocardial ischemia condition, and
   alerting said ambulatory patient of at least one of said distortion patterns.

22. A method according to claim 21, wherein said detecting step includes analyzing at least one of the slope, amplitude, the area, inflection points and sequences of said waveforms for determining whether said waveforms approximate said EKG pattern.

23. The method according to claim 22, wherein said detecting step further includes the step of comparing the slope of said waveforms with a predetermined threshold value for a given period of time.

24. The method according to claim 22, wherein said inflection points are within the range of from 3 to 5 for approximating said EKG signal pattern.

25. The method according to claim 22, wherein said sequence of said waveforms is detected for a given time period of between 125 milliseconds and 2 seconds.

26. The method according to claim 22, wherein said inflection points are within the range of from 3 to 7 for a ventricular premature beat waveform.

27. The method according to claim 21, wherein an average time for successive peaks in said waveforms is computed, and further comprising the step of comparing said average time with a time between a current waveform peak and an immediately preceding waveform peak.

28. The method according to claim 21, wherein a compensatory time interval is computed for the succession of a normal waveform beat and a ventricular premature waveform beat for establishing a reference compensatory pause, and further comprising the step of comparing the time interval between a current succession of waveforms with said reference compensatory pause for determining the presence of an actual compensatory pause, and hence the presence of said ventricular premature waveform beat.

29. The method according to claim 21, including the further step of storing and updating the duration of said linear portions in said waveforms sampled in said sampling step.

30. A method for detecting the significance of slope conditions for a series of complex waveforms in which a computer means and a plurality of shift registers are used for analyzing said waveforms, comprising the steps of:
   calculating a current slope value as the difference between the amplitudes of two successive values in the waveform;

assigning to a first group of shift registers from said plurality of shift registers a value corresponding to the sign value of said current slope value;

comparing the quantitative value of said current slope value with a predetermined threshold value;

assigning to a second group of shift registers from said plurality of shift registers a value corresponding to said quantitative comparison;

assigning a bit from each of said first group of shift registers for said sign value of each said current slope value;

assigning a bit from each of said second group of shift registers for the output of said step of comparing; and updating one of the peripheral bits of each of said registers as a Flag Bit after each sampling period for indicating a trend, or the absence of a trend, in said registers.

31. The method of claim 30, wherein said predetermined slope values comprise a negative slope value, a positive slope value, an active slope value and a quiescent slope value.

32. The method of claim 30, wherein for said current slope value corresponding to a negative value, bits of one register of said first group of registers are shifted to the left and the rightmost bit therein is set to zero, and bits of another register of said first group of registers are shifted to the left and the rightmost bit therein is set to one.

33. The method of claim 30, wherein for said current slope value corresponding to a positive value, bits of one register of said first group of registers is shifted to the left and the rightmost bit therein is set to one, and bits of another register of said first group of registers is shifted to the left and the rightmost bit therein is set to zero.

34. The method of claim 30, wherein for said quantitative value corresponding to a value less than said threshold value, bits of one register of said second group of registers is shifted to the left and the rightmost bit therein is set to zero, and bits of another register of said second group of registers is shifted to the left and the rightmost bit therein is set to one.

35. The method of claim 30, wherein for said quantitative value corresponding to a value equal to or greater than said threshold value, bits of one register of said second group of registers is shifted to the left and the rightmost bit therein is set to one, and bits of another register of said second group of registers is shifted to the left and the rightmost bit therein is set to zero.

36. The method of claim 30, wherein said predetermined threshold value corresponds to 0.02 millivolt change in each 256th part of a second during the sampling period.

37. The method of claim 32, wherein the status of said Flag Bit is determined as a function of the number of ones in each of said shift register bits arrayed in each shift register.

38. The method of claim 33, wherein the status of said Flag Bit is determined as a function of the number of ones in each of said shift register bits arrayed in each shift register.

39. The method of claim 34, wherein the status of said Flag Bit is determined as a function of the number of ones in each of said shift register bits arrayed in each shift register.

40. The method of claim 35, wherein the status of said Flag Bit is determined as a function of the number of ones in each of said shift register bits arrayed in each shift register.

* * * * *

UNITED STATES PATENT AND TRADEMARK OFFICE
CERTIFICATE OF CORRECTION

PATENT NO. : 4,679,144
DATED : July 7, 1987
INVENTOR(S) : MICHAEL W. COX et al

Page 1 of 3

It is certified that error appears in the above-identified patent and that said Letters Patent is hereby corrected as shown below:

IN THE ABSTRACT:

Line 8, "arrhythemia" should read --arrhythmia--.

IN THE DRAWINGS:

Sheet 1, Fig. 3, the legend for block 300 should read --VPB VERIFICATION I--;

Fig. 3, the legend for block 500 should read --VPB VERIFICATION II--.

IN THE SPECIFICATION:

Column 1, line 8 of first paragraph, "arrhythemia" should read --arrhythmia--;

line 7 of second paragraph, "symtoms" should read --symptoms--;

second line from bottom, "betaadrenergic" should read --beta-adrenergic--.

Column 4, line 15, "shft" should read --shift--.

UNITED STATES PATENT AND TRADEMARK OFFICE
CERTIFICATE OF CORRECTION

PATENT NO. : 4,679,144
DATED : July 7, 1987
INVENTOR(S) : MICHAEL W. COX et al

It is certified that error appears in the above-identified patent and that said Letters Patent is hereby corrected as shown below:

Column 5, line 28, "tro-to-patient" should read
--trode-to-patient--.

Column 6, line 27, "shows the the logic" should read
--shows the logic--;

line 40, "up to, but no exceeding," should read
--up to, but not exceeding,--;

line 45, "waveform form" should read --waveform--.

Column 7, subtitle following line 25 should read
--QRS Verification Block 400--;

line 62, "shorter that" should read --shorter than--.

Column 8, ninth line from bottom, "compare" should read
--compares--.

Column 9, fourth line from bottom, "If, within, the" should
read --If, within the--.

Column 10, line 56, "and" at beginning of line should be
deleted.

UNITED STATES PATENT AND TRADEMARK OFFICE
CERTIFICATE OF CORRECTION

PATENT NO. : 4,679,144
DATED : July 7, 1987
INVENTOR(S) : MICHAEL W. COX et al

It is certified that error appears in the above-identified patent and that said Letters Patent is hereby corrected as shown below:

IN THE CLAIMS:

Claim 1, line 9, "stracting" at the beginning of the line should read --tracting--.

Claim 2, line 4, "occurence" should read --occurrence--.

Claim 3, line 1, "monitir" should read --monitor--.

Claim 6, line 12, "instruments" should read --instructions--.

Claim 10, line 5, "comprises" should read --comprising--.

Signed and Sealed this

Tenth Day of May, 1988

*Attest:*

DONALD J. QUIGG

*Attesting Officer*   *Commissioner of Patents and Trademarks*